US00PP35479P2

(12) United States Plant Patent
Miller

(10) Patent No.: US PP35,479 P2
(45) Date of Patent: Nov. 14, 2023

(54) ***LEUCADENDRON* PLANT NAMED 'AFTERBURNER'**

(50) Latin Name: *Leucadendron salignum x discolor*
Varietal Denomination: AFTERBURNER

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 17/734,635

(22) Filed: May 2, 2022

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 5/00; A01H 5/02
See application file for complete search history.

(56) References Cited

PUBLICATIONS www.montereybaynsy.com/L.htm; Apr. 22, 2023; 3 pages.*
www.facebook.com/montereybaynursery/; May 11, 2021; 3 pages.*

* cited by examiner

*Primary Examiner* — Kent L Bell
(74) *Attorney, Agent, or Firm* — Cassandra Bright

(57) ABSTRACT

A new and distinct *Leucadendron* cultivar named 'AFTERBURNER' is disclosed, characterized by a distinctively low and compact plant habit. Plants are strongly branched with many sprays of flower heads. Floral bracts are creamy yellow with a rosy apical flush. Resistance to root rot has been observed in the new variety. The new cultivar is a *Leucadendron*, typically suited for ornamental garden use.

1 Drawing Sheet

Latin name of the genus and species: *Leucadendron salignum* x *discolor.*

Variety denomination: 'AFTERBURNER'.

BACKGROUND OF THE INVENTION

The new variety is the result of crossings conducted during the Winter of 2012 by the inventor, Luen Miller in Royal Oaks, CA. Seed was bulk collected from crossing blocks of various unpatented varieties of *Leucadendron salignum* and *Leucadendron discolor.* The exact parents cannot be identified. The new variety 'Afterburner' was selected during the Spring of 2017 at a commercial nursery in Royal Oaks, California.

After selecting and isolating the new cultivar, asexual reproduction of the new cultivar 'AFTERBURNER' was first performed at a commercial nursery in Royal Oaks, California in March of 2019. Semi-softwood vegetative terminal cuttings were used for propagation. The inventor continued confidential, controlled evaluation and propagation of 'AFTERBURNER'. 'AFTERBURNER' has since produced multiple generations and has shown that the unique features of this cultivar are stable and reproduced true to type. Typical asexual reproduction of the new variety is by softwood vegetative cuttings.

SUMMARY OF THE INVENTION

The cultivar 'AFTERBURNER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AFTERBURNER.' These characteristics in combination distinguish 'AFTERBURNER' as a new and distinct *Leucadendron* cultivar:

1. Low, compact habit.
2. Strongly branched, with many sprays of flower heads.
3. Striking creamy yellow floral bracts with a rosy apical flush.
4. Conspicuous yellow and red flower clusters
5. Improved resistance to root rot compared to known *Leucadendron* varieties.

PARENTAL COMPARISON

Exact parents cannot be identified.

COMMERCIAL COMPARISON

Plants of the new cultivar 'AFTERBURNER' can be compared to the commercial variety *Leucadendron* 'Little Bit', unpatented. Plants of 'AFTERBURNER' are similar to plants of 'Little Bit' in most horticultural characteristics, however, plants of 'AFTERBURNER' differ in the following:

1. Flower heads and bracts of 'AFTERBURNER' are larger than those of 'Little Bit'.
2. Plants of 'AFTERBURNER' are more compact than plants of 'Little Bit'.
3. The new variety is denser, with more vigorous branching than plants of 'Little Bit'.
4. Plants of 'AFTERBURNER' have exhibited improved resistance to root rot compared to plants of 'Little Bit'.

Plants of the new cultivar 'AFTERBURNER' can be compared to *Leucadendron* 'Winter Red', unpatented. The new variety is similar in some horticultural characteristics. However, plants of 'AFTERBURNER' differ in the following:

1. Foliage of the new variety is longer and narrower than foliage of this comparator.
2. Flowering bract color of the new variety is creamy yellow with a rosy apical flush; bract color of 'Winter Red' is deep red.
3. New growth of the new variety is lighter in color than that of 'Winter Red'.
4. Plants of the new variety are more vigorous than plants of 'Winter Red'.
5. Plants of the new variety are more open and less dense than plants of 'Winter Red'.

BRIEF DESCRIPTION OF THE PHOTOGRAPH

The accompanying photograph was taken using conventional techniques and although colors may appear different from actual colors due to light reflectance it is as accurate as possible by conventional photographic techniques. The photograph depicts a flowering plant of 'Afterburner' at approximately 1.5 years, in a 1-gallon pot.

DETAILED BOTANICAL DESCRIPTION

In the following description, color references are made to The Royal Horticultural Society Colour Chart, 2007, except where general terms of ordinary dictionary significance are used. The following observations and measurements describe 'AFTERBURNER' plants grown at a commercial nursery in Royal Oaks, California, under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Leucadendron salignum* x *discolor* 'AFTERBURNER'.

Age of the plant described: Approximately 2 years.

Container size of the plant described: 1-gallon commercial container.

PROPAGATION

Propagation method: Terminal cuttings, hardwood or semi-softwood.

Time to develop roots suitable for transplanting: About 6 to 8 weeks at an average temperature around 25° C.

Root description: Woody, not well branched, colored near Brown N199A and Grey-Brown 199A and 199B. Typically shallow rooted.

PLANT

Growth habit: Compact shrub. Irregular globular shape.

Height: 30 cm.

Plant spread: 25 cm.

Plant vigor: Moderate.

Branching characteristics: A pinched plant produces 3 to 5 main lateral branches on average.

Stem description:

*Shape*.—Round.

*Length*.—Approximately 5 cm before pinch.

*Diameter*.—About 1.0 cm.

*Texture*.—Glabrous, striated. No scales, bark or lenticels observed.

*Strength*.—Very strong.

*Color*.—Near RHS Greyed-Red 183C, with fine striations colored near Greyed-Green 198C.

*Internode length*.—Average 5 cm.

Lateral branches:

*Shape*.—Round.

*Length of primary lateral branches*.—Average range 10 to 12 cm.

*Diameter of lateral branches*.—Approximately 4 mm.

*Approximate quantity of lateral branches*.—An average of 6 lateral branches emerge at the location of each terminal inflorescence after flowering is completely ended.

*Branching arrangement*.—Whorled.

*Texture*.—Fine pubescence and striation.

*Color*.—Mature: Greyed-Purple 183C. Immature: Upper surface near Greyed-Purple 187C. Lower surface near Yellow-Green 144C heavily flushed near Greyed-Purple 187C.

*Internode length*.—Average 0.5 cm to 1.5 cm.

FOLIAGE

Leaf:

*Arrangement*.—Spiral.

*Quantity*.—Approximately 24 to 32, per main branch, including sub-branches.

*Average length*.—3.0 cm to 4.5 cm.

*Average width*.—5 mm to 10 mm.

*Shape of blade*.—Oblanceolate.

*Apex*.—Acute.

*Base*.—Tapered.

*Margin*.—Entire. Dense, short pubescence.

*Texture of top surface*.—Short pubescence.

*Texture of bottom surface*.—Short pubescence.

*Aspect*.—Concave. Youngest foliage flat.

*Color*.—Young foliage upper side: Near RHS Green 137A. Young foliage under side: Near RHS Green 137A. Mature foliage upper side: Near RHS Green 139A. Mature foliage under side: Near RHS Green 137A.

*Foliage fragrance*.—None.

*Leaf internode*.—5 mm.

*Venation*.—Type: Pinnate. Venation color upper side: Indistinguishable from foliage coloration. Venation color under side: Indistinguishable from foliage coloration.

*Petiole*.—No present, sessile.

FLOWER

Natural flowering season: Winter.

Inflorescence type and habit: Male only flowers. Minute flowers occurring in spiraling rows on conical spikes. Flowers tubular structure of fused petals, outwardly facing. Flower self-cleaning, persisting approximately 8 to 12 weeks on the spike.

Quantity of flowers per inflorescence: 150 to 240 occurring in 8 or 12 rows of 20 to 40 flowers.

Inflorescence size:

*Diameter*.—Approximately 1.8 cm.

*Height*.—Approximately 2.0 cm.

Inflorescence longevity: Ornamental for approximately 4 months. After 6 months inflorescence has completely shrunken and dried and been covered by new lateral branches.

Individual flowers:

*Size*.—Diameter: Approximately 1 mm. Length: Approximately 2 to 3 mm.

*Shape*.—Tubular.

Petals:

*Petal arrangement*.—Spiral.

*Shape*.—Fused, tubular.

*Size*.—Length: about 0.5 mm. Width: about 0.3 mm.

*Margin*.—Entire.

*Apex*.—Rounded.

*Base*.—Fused.

*Petal quantity*.—Indistinguishable, single, minute structure.

*Texture*.—Glabrous.

Flower color, described as a single structure, as there are no distinguishable upper and lower surfaces:

*Apical flowers*.—When opening: Near RHS Yellow-Green N144A very heavily flushed Orange-Red N34A. Fully opened: Near RHS Orange-Red N34A.

*Main inflorescence flowers*.—When opening: Near RHS Yellow 12B flushed Yellow-Green N144A. Fully opened: Near RHS Yellow 13A.

Bud:

*Shape*.—Ovate.

*Length*.—Approximately 0.8 mm.

*Diameter*.—Approximately 0.4 mm.

*Color*.—Apical buds: Near RHS Yellow-Green N144A flushed Orange-Red N34A. Main inflorescence buds: Near RHS Yellow-Green N144A flushed Yellow 12B.

Fragrance: Musty.

Involucral bracts:

*Number*.—Average range 4 to 8.

*Length*.—Approximately 10 to 20 mm.

*Width*.—Approximately 3 to 5 mm.

*Shape*.—Linear.

*Texture*.—Glabrous.

*Apex shape*.—Acute.

*Base*.—Truncate.

*Margin*.—Entire.

*Color*.—Near RHS Yellow 7D. Apex near Red-Purple 59B. Marginal flush near 59C, strongest near apex.

Floral bracts:

Description: Leaf like, occurring just below inflorescence.

*Quantity*.—Average range 9 to 16.

*Arrangement*.—Spiral.

*Average length*.—3.0 cm to 4.5 cm.

*Average width*.—6 to 8 mm.

*Shape of blade*.—Oblanceolate.

*Apex*.—Acute.

*Base*.—Truncate.

*Margin*.—Entire.

*Texture of top surface*.—Glabrous.

*Texture of bottom surface*.—Glabrous.

*Pubescence*.—None.

*Aspect*.—Very slightly concave.

*Angle of attachment*.—About 45°.

*Color*.—Immature: Upper surface: Near Yellow 2D. Faint Central flush near Yellow-Green 144C. Very thin margin near Red-Purple 59B. Apex 59A. Under surface: Near Yellow 2D. Faint Central flush near Yellow-Green 145A. Very thin margin near Red-Purple 59B. Apex 59A. Mature: Upper surface: Near Yellow 4B. Faint central streak near Yellow-Green 144C. Margin near Red-Purple 59B. Apex 59A. Flushing upper ⅓ colored near 59B. Under surface: Near Yellow 4B. Faint central streak near Yellow-Green 144C. Margin near Red-Purple 59B. Apex 59A. Flushing upper ⅓ colored near 59B.

Peduncle: Beginning from the lateral branch to lowermost floral bract.

*Length*.—Approximately 6 cm to 8 cm.

*Diameter*.—Approximately 3 to 4 mm.

*Texture*.—Glabrous.

*Color*.—Upper surface near Greyed-Purple 187C. Lower surface near Yellow-Green 144C heavily flushed near Greyed-Purple 187C.

REPRODUCTIVE ORGANS

Minute flowers with compressed reproductive organs. Reproductive organs not visible under a dissecting microscope. Abundant pollen colored near Yellow 13A.

OTHER CHARACTERISTICS

Seeds and fruits: No seeds/fruits observed.

Disease/pest resistance: Observed improved resistance to root rot diseases of *Leucadendron*. The primary root rot disease is *Phytophthora cinnamomi*. No other resistance nor susceptibility to normal pests and diseases of *Leucadendron* has been observed.

Temperature tolerance: USDA Zone 9.

What is claimed is:

1. A new and distinct cultivar of *Leucadendron* plant named 'AFTERBURNER' as herein illustrated and described.

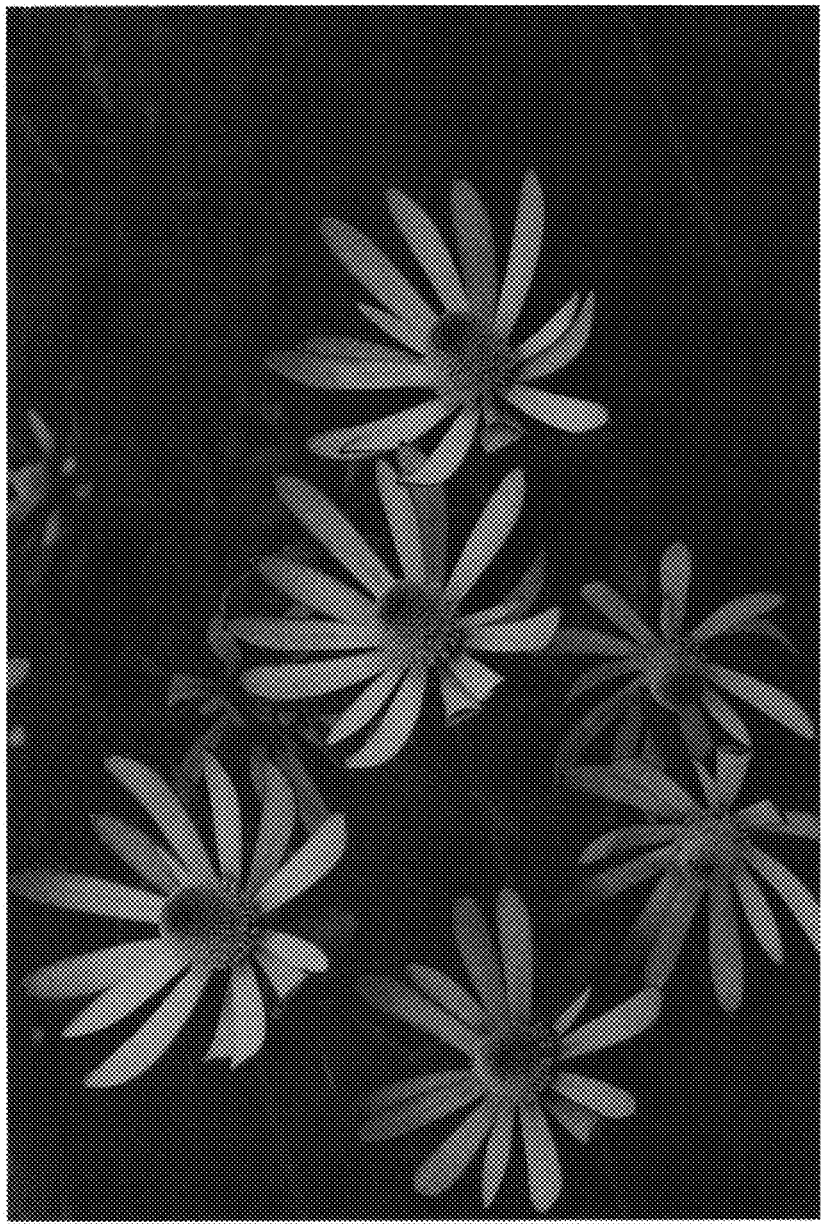

* * * * *